United States Patent [19]

Byrne

[11] Patent Number: 5,307,805
[45] Date of Patent: May 3, 1994

[54] SURGICAL RETRACTOR ASSEMBLY

[75] Inventor: Donny M. Byrne, Conroe, Tex.

[73] Assignee: Surgical Innovations I, L.P., Conroe, Tex.

[21] Appl. No.: 911,482

[22] Filed: Jul. 10, 1992

[51] Int. Cl.⁵ .............................................. A61B 17/02
[52] U.S. Cl. ........................................ 128/20; 128/3; 604/158; 606/198
[58] Field of Search ............. 128/3, 20, 61; 604/158, 604/164, 165, 167, 263, 264; 606/167, 185, 198, 205

[56] References Cited

U.S. PATENT DOCUMENTS

| | | | |
|---|---|---|---|
| 4,226,228 | 10/1980 | Shin et al. | 128/23 |
| 4,239,036 | 12/1980 | Krieger | 128/20 |
| 4,654,030 | 3/1987 | Moll et al. | 604/165 |
| 4,777,939 | 10/1988 | Kees, Jr. | |
| 4,802,479 | 2/1989 | Haber et al. | |
| 5,029,573 | 7/1991 | Chow | |
| 5,139,487 | 8/1992 | Baber | 604/165 |
| 5,152,279 | 10/1992 | Wilk | 128/17 |

Primary Examiner—C. Fred Rosenbaum
Assistant Examiner—N. Kent Gring
Attorney, Agent, or Firm—Harrison & Egbert

[57] ABSTRACT

A retractor instrument assembly having a sleeve with a non-circular cross-sectional shape, an elongated rod slidably received within the sleeve, and a plurality of blades foldably connected together at an end of the elongated rod. The elongated rod has a handle at one end. The blades are hingedly connected to the rod at the end opposite the handle. The blades are movable between a folded configuration and an unfolded configuration. The folded configuration assumes a position which is slidable within the sleeve. The sleeve has a passageway with a triangular cross-section. The blades are of a generally triangular configuration when in the folded position. The plurality of blades includes a first blade connected to the rod, a second blade resiliently connected to one side of the first blade, and a third blade resiliently connected to an opposite side of the first blade. A remote actuator is provided so as to angularly displace the blades relative to the elongated rod.

19 Claims, 3 Drawing Sheets

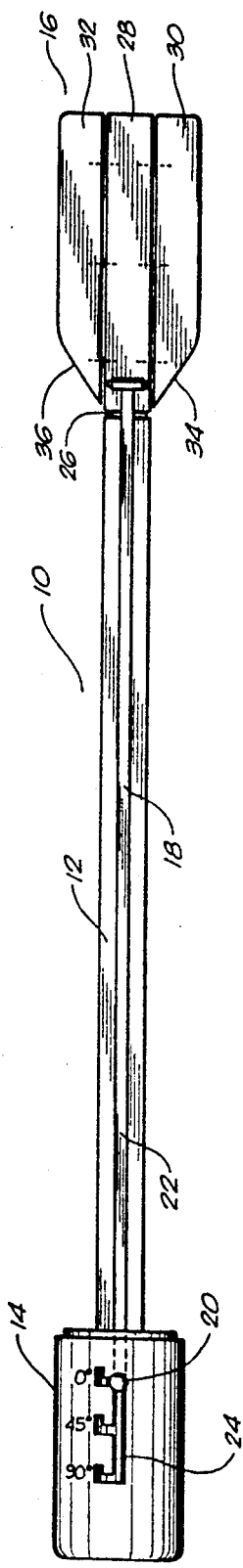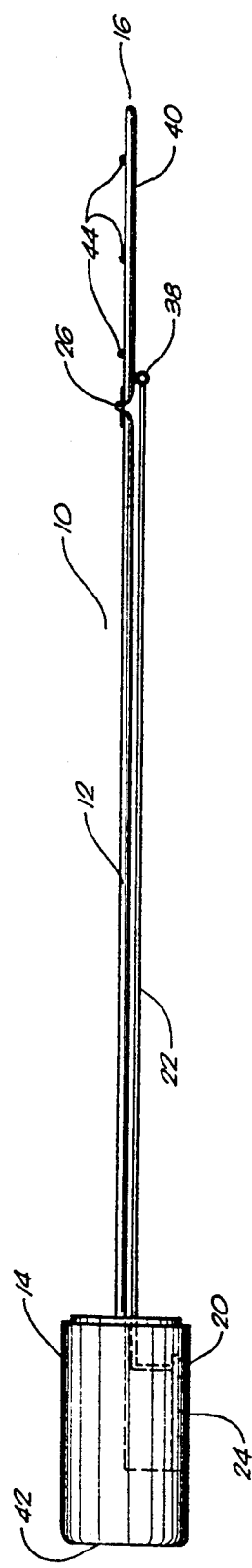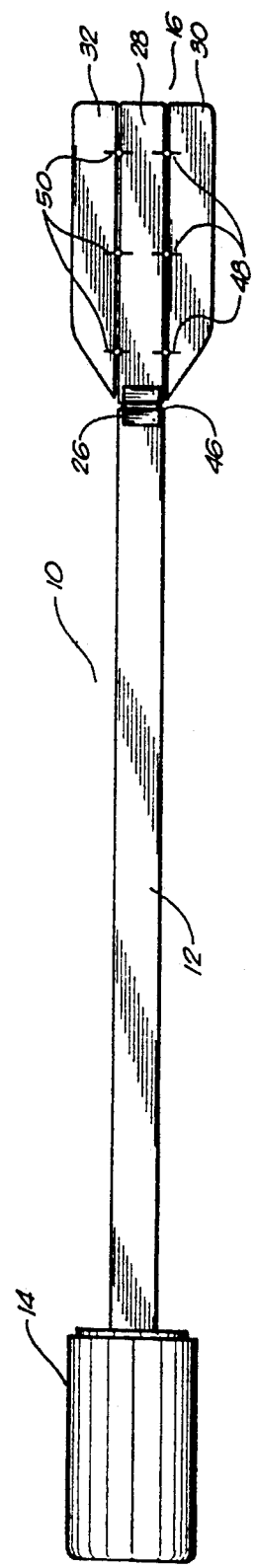

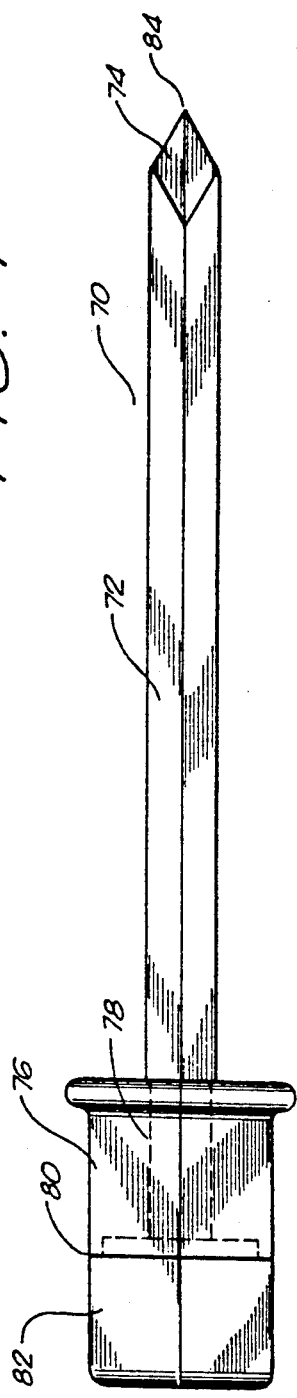
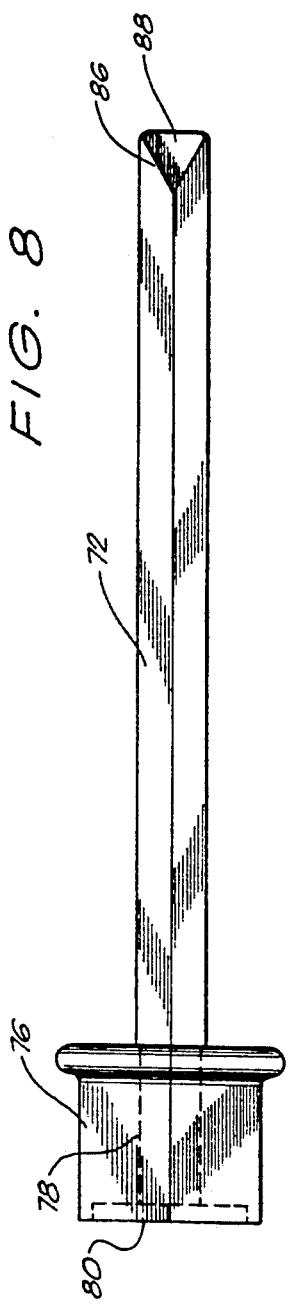
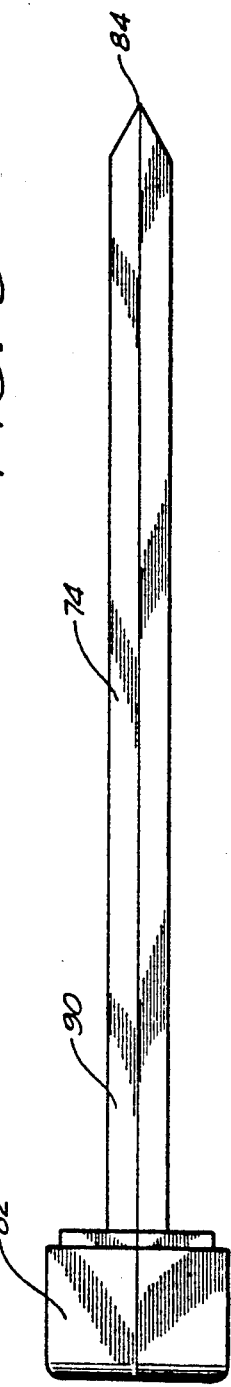
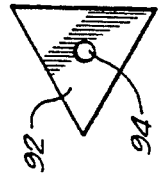

SURGICAL RETRACTOR ASSEMBLY

TECHNICAL FIELD

The present invention relates to surgical retractor assemblies, in general. More particularly, the present invention relates to surgical retractors that are used for laparoscopy and are extended through a trocar sleeve.

BACKGROUND ART

Laparoscopy is a general term referring to the use of a laparoscope, a device consisting of a tube and an optical system, for exploring the peritoneal cavity or performing surgical procedures. A laparoscope is a specific type of endoscope, which is a device for viewing a body cavity or organ through a natural orifice or through a surgical incision.

The equipment used in laparoscopy normally includes a trocar. A trocar is a hollow steel tube with a pyramid-shaped point at one end. The trocar will fit into a sleeve or cannula, which has a valve at the other end. The equipment used in a laparoscopy also includes an optical system of lenses and eyepieces for viewing, a fiberoptic light system for lighting the operative field, a gas insufflation apparatus to inflate the peritoneal cavity so as to enhance the surgeon's ability to see inside the cavity, and other attachments such as scissors, forceps, electrodes, and electrocautery devices.

Laparoscopy can be performed under general anesthesia or under local anesthesia with mild sedation. Since diagnostic laparoscopy involves extensive manipulation of tender pelvic organs, local anesthesia is not recommended for those procedures. After the patient is positioned in the stirrups, the table is tilted slightly to place the patient in a modified Trendelenburg position. A clear gas, either carbon dioxide or nitrous oxide, is then pumped into the peritoneal cavity through a special needle. The needle is then removed and the incision is enlarged to about one centimeter. The trocar and sleeve are then inserted through the enlarged incision, the trocar is removed, and the laparoscope itself, along with its attachments, is inserted through the sleeve. Sometimes a two-incision technique is used in order to fully visualize the entire abdominal area or to insert a second instrument, such as a retractor. After the procedure, the instruments are removed from the sleeve, and the valve on the sleeve is opened to let the gas out.

In those situations in which a retractor used in the two-incision approach to laparoscopy, the retractor will be inserted through another sleeve in the abdominal cavity. One of the common problems associated with the use of retractors in laparoscopy is the fact that the end of the retractor, which enters the abdominal cavity, is generally smaller than the diameter of the sleeve through which it passes. As such, the retractor has a relatively small surface area within the abdominal cavity that must be used for the manipulation of organs within the abdomen. Since the retractors must be of relatively small diameter, in order to pass through the sleeve, there is the general inability to properly manipulate the organs so as to enhance the ability to carry out the viewing process. Many times, surgeons are generally apprehensive to the use of such retractors during the surgery. The small diameter retractor can potentially puncture the bowels, or other internal organs, during the manipulation within the cavity.

The ability to manipulate the organs during the two-incision process of laparoscopy greatly enhances the ability of the surgeon to properly tend to the needs of the patient. Unfortunately, many retractors, which are used in the surgical procedure, are rigid implements that can only carry out one-dimensional movements within the abdominal cavity. Since the ends of the retractors, within the cavity, are fixed, the only way to manipulate the end is to manipulate the retractor, and the sleeve, within the incision. This has been found to be ineffective for the needs of laparoscopy.

It is an object of the present invention to provide a surgical retractor assembly for use in laparoscopy procedures.

It is another object of the present invention to provide a surgical retractor assembly that provides a maximum of surface area within the abdominal cavity.

It is another object of the present invention to provide a surgical retractor that is remotely actuable so as to enhance the ability to manipulate internal organs.

It is still a further object of the present invention to provide a surgical retractor assembly that is easy to use, and adaptable to a wide variety of situations.

These and other objects and advantages of the present invention will become apparent from a reading of the attached specification and appended claims.

SUMMARY OF THE INVENTION

The present invention is a retractor instrument assembly which comprises an elongated rod having a handle at one end, a first blade extending outwardly from an end of the elongated rod opposite the handle, and a second blade foldably connected to one side of the first blade. A third blade is foldably connected to an opposite side of the first blade. The second and third blades are movable between a first position in planar alignment with the first blade and a second position forming a triangular configuration with the first blade. The second and third blades are in resilient connection with the first blade. This resilient connection urges the second and third blades into the first position.

The ends of the second and third blades are in linear alignment with the end of the first blade opposite the elongated rod. The second and third blades have an angled surface extending from an end of the elongated rod. The narrow end of the angled surface is adjacent to the first blade. The first blade is hingedly connected to the elongated rod.

The present invention also includes a suitable remote actuator which is interconnected to the first blade so as to angularly displace the first blade relative to the rod. This remote actuator includes a slide actuator which is positioned on the handle, and is movable on the handle, and a control rod that is connected to the actuator at one end and to the first blade at another end such that a movement of the actuator causes an angular movement of the first blade relative to the elongated rod. The first blade is movable between a first position in linear alignment with the elongated rod and a second position extending transverse to the elongated rod.

The present invention further includes a sleeve which extends around the elongated rod. The sleeve has a passageway having a triangular cross-sectional configuration. This interior triangular cross-sectional configuration has a sufficient size so as to slidably receive the second and third blades when they are in their second position. The sleeve has an end opposite to the handle which has an angularly offset opening.

A trocar member is provided which is slidably received within the passageway of the sleeve. The trocar member has one pointed end extending outwardly through one end of the sleeve. The trocar number has a handle at an end opposite to the pointed end. This handle extends outwardly from another end of the sleeve. The trocar member also has a triangular cross-sectional shape within the passageway of the sleeve.

A spacer member is provided which is removably fastened to an end of the sleeve. The spacer member serves to provide for a valved sealing of an interior of the sleeve.

BRIEF DESCRIPTION OF THE DRAWINGS

FIG. 1 is a plan view of the retractor instrument in accordance with the preferred embodiment of the present invention.

FIG. 2 is a side elevational view of the retractor instrument in accordance with the preferred embodiment of the present invention.

FIG. 3 is a bottom view of the retractor instrument in accordance with the preferred embodiment of the present invention.

FIG. 7 is a side elevational view of the trocar assembly of the present invention.

FIG. 8 is a side elevational view of the sleeve in accordance with the present invention.

FIG. 9 is a side elevational view of the trocar member of the present invention.

FIG. 10 is an isolated view showing the spacer as used in the present invention.

DETAILED DESCRIPTION OF THE INVENTION

Figure 4:
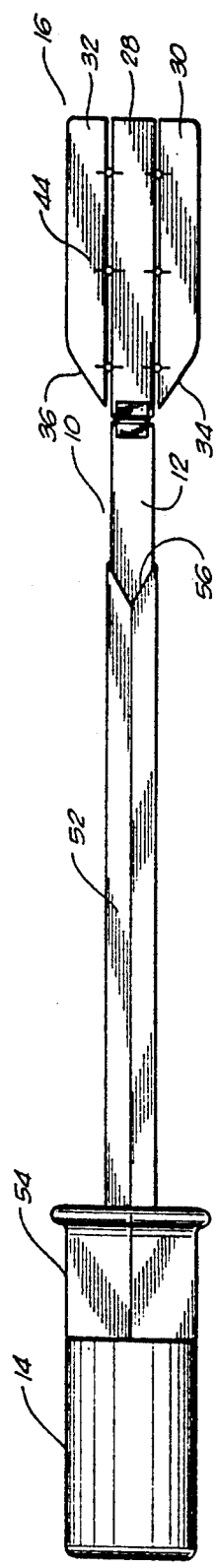
FIG. 4 is a bottom view of the assembly of the present invention showing the retractor instrument extending through a sleeve.

Referring to FIG. 1, there is shown at 10 the retractor instrument in accordance with the preferred embodiment of the present invention. Retractor instrument 10 includes an elongated rod 12, a handle 14, a plurality of blades 16, and a remote actuator 18. Each of these elements cooperate so as to provide a retractor instrument 10 which enhances the ability to carry out laparoscopic surgery.

The elongated rod 12 is a steel rod made of a laser non-reflective material. The rod 12 extends from handle 14 to the blades 16. In normal use, the rod 12 will extend through a sleeve which enters the human body during laparoscopic surgery. As will be described hereinafter, the elongated rod 12 has a width that is suitable for passing through the sleeve.

The handle 14 is placed at one end of the rod 12. Handle 14 has a suitable size and configuration for manipulation by the surgeon. It can be seen that the handle 14 has a greater diameter then that of rod 12. Handle 14 includes a slide actuator 20 positioned thereon. Slide actuator 20 is connected to the control rod 22 which extends along the length of elongate rod 12. The control rod 22 is connected at the opposite end to the plurality of blades. In normal use, when the slide actuator 20 is moved along the guide pathway 24, the blades 16 will accordingly be moved and rotated about hinge 26. It can be seen that when the slide actuator 20 moves from the position shown in FIG. 1 to the position indicating "90°", then the control rod 22 will cause the blade 16 to rotate about hinge 26.

The blades 16 specifically comprise a first blade 28, a second blade 30, and a third blade 32. The first blade 28 is hingedly connected at 26 to the elongated rod 12. It can be seen that the control rod 22 is pivotally connected to a surface of the first blade 28. The first blade 28 has the second blade 30 foldably connected at one side of the first blade 28. The third blade 32 is foldably connected to an opposite side of the first blade 28. The first blade 28 has a generally rectangular configuration. The second blade 30 and the third blade 32 terminate at the same end of first blade 28 such that the end edges are in linear alignment. Importantly, the second blade 30 and the third blade 32 have angled surfaces 34 and 36, respectively. It can be seen that the angled surfaces 34 and 36 extend from the hinged connection of the first blade 28 to the rod 12. The narrow end of the angled surfaces 34 and 36 are adjacent to the sides of the first blade 28. The angled surfaces 34 and 36 taper outwardly from the control rod 12. The taper shown by angled surfaces 34 and 36 allows for the proper manipulation and control of the blades 16. In FIG. 1, the blades 28, 30, and 32 are shown in their unfolded configuration.

FIG. 2 shows a side view of the retractor instrument 10. Specifically, it can be seen that the elongated rod 12 has a relatively narrow thickness. The blades 16 are shown as being in linear alignment with the rod 12. Blade 16 generally has the same thickness as the rod 12. The handle 14 is a generally cylindrical member which is fastened to the elongated rod 12 from the blades 16. Handle 14 includes the slide actuator 20 which travels in pathway 24. Slide actuator 20 is connected to the control rod 22 for the purposes of remotely manipulating the blades 16. The blades 16 are shown as connected to elongated rod 12 by hinge 26. The control rod 22 is pivotally connected at 38 to the bottom surface 40 of the blades 16. When the slide actuator 20 is moved toward the rear end 42 of the handle 14, the blades 16 will pivot about hinge 26 so as to move from a position in linear alignment with the rod 12 to a position transverse to the rod 12, as will be described hereinafter.

In FIG. 2, it can be seen that the blades 16 are shown in their unfolded condition. The unfolded condition provides a generally flat and wide surface. A plurality of springs 44 are provided as resilient connectors between the blades 28, 30, and 32. In FIG. 2, the springs 44 are shown as positioned on an exterior surface of the blades 16. The springs 44 can also be positioned within the blades 16 for the purpose of providing the resilient connection between the blades.

FIG. 3 shows another view of the retractor instrument 10. Specifically, in FIG. 3, it can be seen that the bottom view of FIG. 3 shows the elongated rod 12, the handle 14, and the blades 16. Importantly, the hinge 26 is illustrated as connected to the end 46 of rod 12 and to an adjacent end of the first blade 28. The second blade 30 is connected by resilient spring 48 to the first blade 28. Similarly, the third blade 32 is connected by resilient springs 50 to the first blade 28. The resilient connection between the blades 28, 30 and 32 tends to urge the blades 30 and 32 to spread outwardly in the configuration shown in FIGS. 1-3. As such, the springs 48 and 50 serve to automatically open the plurality of blades 16 when they pass through the end of a sleeve and into the human body. It can be seen in FIGS. 1-3 that the plurality of blades 16 provide a retractor surface that is relatively wide in comparison with the width of the rod 12. As such, there is a greater surface area which is provided for the manipulation of the internal organs. The use of the remote actuator 18 allows for additional manipulation of the retractor surfaces when they are within the human body. The handle 14 will continue to remain outwardly of the end of the sleeve so as to extend outside of the human body.

FIG. 4 shows the retractor instrument 10 as used within a sleeve 52. Sleeve 52 has a head 54 attached to one end of the sleeve 52. As will be described hereinafter, the sleeve 52, along with the passageway formed within the head 54, has a generally triangular cross-sectional configuration. It can be seen that the sleeve 52 has a first end 56 through which the rod 12 of the retractor instrument 10 can pass. The plurality of blades 16 is shown in an unfolded condition beyond the open end 56 of the sleeve 52. Importantly, the open end 56 of the sleeve 52 has an angularly offset triangular-shaped configuration. The surfaces of the opening 56 can be slightly curved so as to cause for the folding of the blade 16 when the retractor instrument 10 is pulled from the position shown in FIG. 4. In addition, the angled surfaces 34 and 36 may be TEFLON (TM) coated so as to facilitate the folding of the second blade 30 and the third blade 32 with respect to the first blade 28.

After the retractor instrument 10 has been used within the abdominal cavity, it is necessary to pull the retractor instrument 10 through the sleeve 52. It appears that this task would be impossible due to the wide flat shape of the blade 16. However, because of the special design of the opening 56, the blades 28, 30, and 32 will fold into a triangular configuration when the angled surfaces 34 and 36 encounter the angled edges of the opening 56. When the handle 14 is pulled, the rod 12 will move rearwardly through the sleeve 52. When the angled surfaces 34 and 36 encounter the angled surfaces of opening 56, then the forces that are applied will cause the second blade 30 and the third blade 32 to overcome the resilient forces of the springs 44 and to form a triangular shape for the purpose of removal through sleeve 52.

Figure 5:
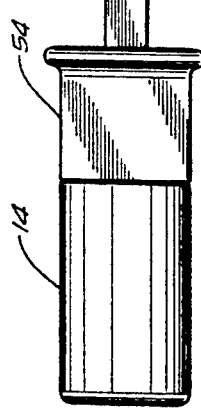
FIG. 5 is a side elevational view of the assembly of the present invention showing, in particular, the manipulation of the blades.

FIG. 5 illustrates the manner in which the retractor instrument 10 allows for the manipulation of the blades 16. Initially, it can be seen that the rod 12 extends outwardly from the end 56 of sleeve 52. The control rod 22 extends below the surface of the elongated rod 12. The rod 12 and the control rod 22 extend through the wide bottom of the triangular cross-sectional shape of the sleeve 52. The end 56 of sleeve 52 has an angularly offset opening. As described hereinbefore, it is this angularly offset opening which allows the blade 16 to fold upon themselves into the triangular configuration.

In FIG. 5, it can be seen that the blades 16 are movable from a position 58 which is in alignment with the elongated rod 12 to a position 60 which is transverse, and at a right angle to, the elongated rod 12. The blade 16 may also assume an intermediate position 62 which is angled at forty-five degrees with respect to the first position 58. These adjustments are carried out by manipulating the slide actuator 20 on the handle 14.

Figure 6:
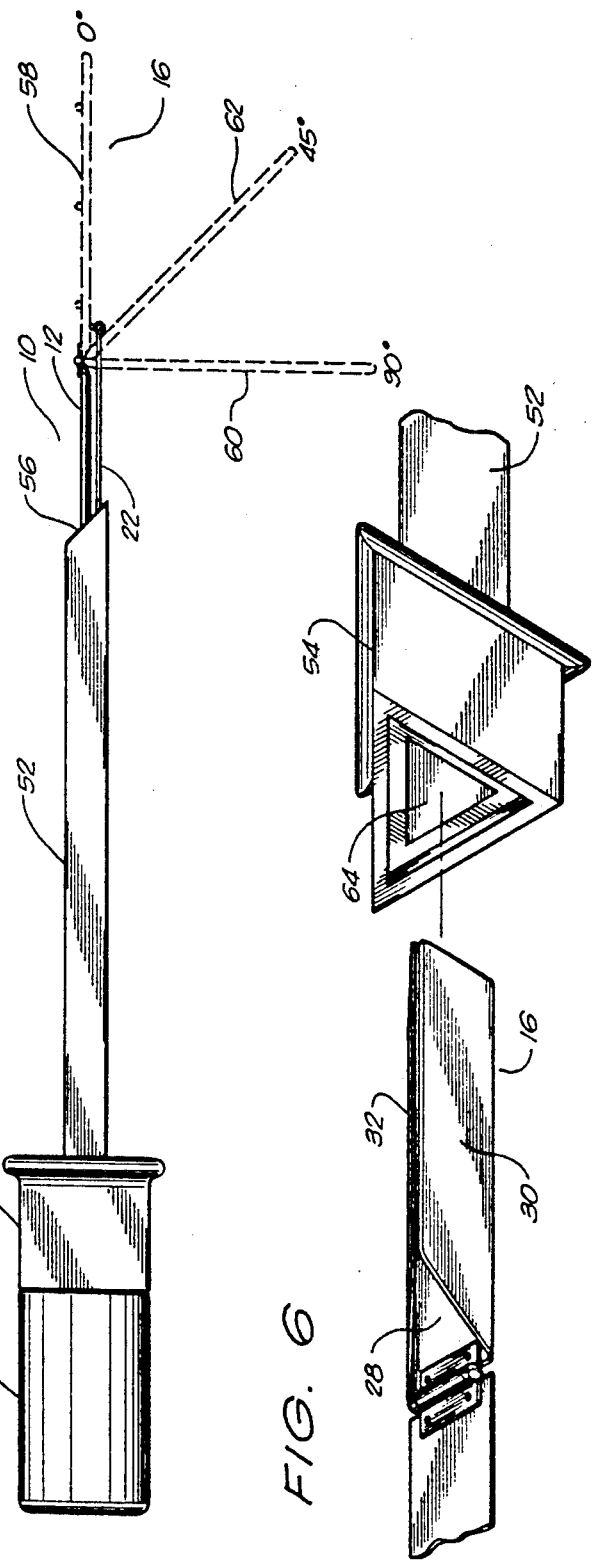
FIG. 6 is an exploded view showing the blades as inserted, in their folded configuration, into the opening of the sleeve.

FIG. 6 shows the manner in which the blades 16 are inserted into the passageway 64 of sleeve 52. As was described hereinbefore, the blades 16 include a first blade 28, a second blade 30, and a third blade 32. When blades 30 and 32 are folded inwardly with respect to the first blade 28, the blades 16 form a triangular configuration. When the blades are in the triangular configuration shown in FIG. 6, they can be easily inserted into the triangular passageway 64 at one end of sleeve 52. The triangular passageway 64 extends through the head 54 of sleeve 52.

In contrast with the prior art, the present invention allows for a wide surface area of the blades 16 as they pass outwardly from the end 56 of the sleeve 52. The prior art retractor used in laparoscopic surgery cannot be expanded after it passes through the opening. Conventionally, trocars, sleeves, and retractors have a circular cross-sectional area. A shape that passes into a circular opening cannot be folded into a convenient shape. As such, the present invention utilizes a non-circular geometric shape for the passageway through the sleeve 52. The wide end of the bottom of the triangular configuration receives the first blade 28 in generally sliding relationship therewith. The second blade 30 and the third blade 32 are folded inwardly in the form of a triangle. As such, the triangular-shaped passageway of sleeve 52 allows for the passage of the blades 16. After they pass outwardly from the end 56 of the sleeve 52, the resilient spring mechanism causes the blades 30 and 32 to unfold so as to create a wide planar surface. A retraction of the instrument through the end 56 of the sleeve 52 creates a folding motion upon the angled surfaces 34 and 36 of the blades 30 and 32. The blades 16 then assume a triangular configuration suitable for passing through the triangular passageway of the sleeve 52.

The present invention further contemplates a trocar assembly 70 as illustrated in FIG. 7. FIG. 7 shows the sleeve 72 and the trocar member 74 extending through sleeve 72. Initially, the sleeve 72 has the configuration described hereinbefore in connection with sleeve 52 of FIGS. 4-6. In particular, the sleeve 72 has a triangular cross-sectional interior passageway and a head 76. It can be seen that the interior passageway 78 extends through the widened head 76 such that it opens at end 80.

The trocar member 74 is a solid member having a handle 82 at one end and a pyramid-shaped pointed end 84 at the opposite end. The trocar member 74 has a triangular configuration suitable for passing through the triangular interior of the sleeve 72. In normal use, the trocar member 74, in combination with sleeve 72, is used so as to create the opening into the abdominal cavity.

FIG. 8 shows an isolated view of sleeve 72. It can be seen that sleeve 72 has an angularly offset end 86 and defines a triangular shaped passageway 88. Passageway 88 allows for the passage of the pointed end 84 of the trocar member 74 and also allows for the passage of blades 16 of the retractor instrument described hereinbefore. The head 76 has the interior opening 78 opening at end 80. End 80 is suitable for abutment with the handle 82 of the trocar member 74.

FIG. 9 shows an isolated view of the trocar member 74. Trocar member 74 has a triangular cross-sectional shape. Pointed end 84 is formed in one end and handle 82 is attached to the opposite end of the trocar member 74. Trocar member 74 has an elongated body 90 which is retained within the interior of the elongated sleeve 72. Specifically, the triangular interior configuration of sleeve 72 slidably receives the body 90 of trocar member 74.

After the trocar assembly 70 of the present invention is used for the creation of opening into the abdomen, the trocar member 74 is slidably removed from sleeve 72. When the trocar member 74 is removed, then the sleeve 72 is suitable for the receipt of the retractor instrument 10. Alternatively, the end 80 of the head 76 can be sealed with a spacer 92. Spacer 92 is a rubberized member that is suitable for fitting within the triangular opening 78 of the sleeve 72. The spacer 92 is a rubberized member that provides valve communication with the interior 78 of the sleeve 72. In normal usage, the valve hole 94 of triangular spacer 92 can receive certain instruments therethrough. For example, if it is desired to inflate the abdominal cavity, then a suitable apparatus can be inserted through the hole 94 of spacer 92 so as to pump air, or other gases, into the abdominal cavity. The spacer 92 prevents the leakage of the gases from the interior of the abdominal wall. The triangular shape of spacer 92 is particularly adapted to the improved configuration of the sleeve 92 of the present invention.

The present invention provides for an improved retractor instrument assembly which significantly improves the ability to carry out laparoscopic surgery. The blades of the retractor assembly provide a wider surface area in which to manipulate internal organs. Additionally, the fear of potential injury by the retractor is minimized by the fact that a wide retractor arrangement (without sharp edges) is used. The smooth rounded edges of the blades 16 further enhances the ability to prevent internal injury during use. The retractor blades of the present invention allows for manipulation of the blade so as to more easily grasp or move the internal organs. The retractor blades can be appropriately manipulated by the use of the slide actuator on the handle of the retractor instrument. The use of the triangular sleeve enables the use of the foldable blade arrangement.

The foregoing disclosure and description of the invention is illustrative and explanatory thereof. Various changes in the details of the illustrated construction may be made within the scope of the appended claims without departing from the true spirit of the invention. The present invention should only be limited by the following claims and their legal equivalents.

I claim:

1. A retractor instrument assembly comprising:
   an elongated rod having a handle at one end;
   a first blade extending outwardly from an end of said elongated rod opposite said handle, said first blade having a first lengthwise edge and a second lengthwise edge;
   a second blade foldably connected by a resilient member to said first lengthwise edge of said first blade; and
   a third blade foldably connected by another resilient member to a second lengthwise edge of said first blade, said second and third blades movable between a first position in flat planar alignment with said first blade to a second position forming a triangular cross-sectional configuration with said first blade.

2. The assembly of claim 1, said resilient members being springs, said springs urging said second and third blades to said first position.

3. The assembly of claim 2 said second and third blades having a first end surface in linear alignment with an end surface of said first blade opposite said handle.

4. The assembly of claim 2, each of said second and third blades having an angled surface adjacent to an end of said elongated rod, a narrow end of said angled surface being adjacent said first blade.

5. A retractor instrument assembly comprising:
   an elongated rod having a handle at one end;
   a first blade extending outwardly from an end of said elongated rod opposite said handle, said first blade having a lengthwise edge, said first blade hingedly connected to said rod;
   a second blade foldably connected by a resilient member to said lengthwise edge of said first blade; and
   remote actuation means interconnected to said first blade, said remote actuation means angularly displacing said first blade relative to said rod.

6. The assembly of claim 5, said remote actuation means comprising:
   an actuator positioned on said handle, said actuator movable on said handle; and
   a control rod connected to said actuator at one end and to said first blade at another end such that a movement of said actuator causes an angular movement of said first blade relative to said elongated rod.

7. The assembly of claim 5, said first blade movable between a first position in linear alignment with said elongated rod and a second position extending transverse to said elongated rod.

8. The assembly of claim 1, further comprising:
   a sleeve extending around said elongated rod, said sleeve having a passageway of a triangular cross-section.

9. The assembly of claim 8 said passageway of said sleeve having a cross-sectional area of sufficient size so as to slidably receive said second and third blades in said second position.

10. The assembly of claim 9, said sleeve having an end opposite said handle, said end having an angularly offset opening.

11. A retractor instrument assembly comprising;
    a sleeve having a passage way of a non-circular cross-sectional shape;
    an elongated rod slidably and removably received within said passageway of said sleeve, said elongated rod having a handle at one end; and
    a plurality of blades foldably and resiliently connected together along lengthwise edges at an end of said elongated rod opposite said handle, said blades movable between a folded configuration and an unfolded configuration, said foldable configuration slidable within said passageway, said unfolded configuration forming a flat planar surface.

12. The assembly of claim 11, said passageway having a triangular cross-section, said plurality of blades having a generally triangular cross-sectional configuration in said folded configuration.

13. The assembly of claim 12, said plurality of blades comprising:
    a first blade connected to said elongated rod, said first blade having a first lengthwise edge and a second lengthwise edge;
    a second blade connected by a resilient member to said first lengthwise edge of said first blade; and
    a third blade connected by another resilient member to said second lengthwise edge of said first blade, said resilient members for urging said blades into said unfolded configuration.

14. The assembly of claim 12, said sleeve having an angularly offset open end adjacent said plurality of blades, said open end for engaging said plurality of blades so as to move said plurality of blades to said folded configuration.

15. The assembly of claim 11, further comprising:

a remote actuator means interconnected to said handle, said remote actuation means connected to said plurality of blades for angularly displacing said blades relative to said elongated rod, said blades in hinged connected to said elongated rod.

16. The assembly of claim 15, said remote actuation means comprising:

slide actuator positioned on said handle, said slide actuator movable on said handle;

a control rod connected to said slide actuator at One end and to at least one of said plurality of blades at another end such that a movement of said slide actuator causes an angular movement of said plurality of blades between a first position in linear alignment with said elongated rod and a second position in transverse relation to said elongated rod.

17. A trocar assembly comprising:

a sleeve having a passageway with a continuously triangular cross-section, said sleeve being an elongated member having said passageway opening at opposite ends of said sleeve; and a trocar member slidably received within said passageway of said sleeve, said trocar member having one pointed end extending outwardly to one end of said sleeve, said trocar member having a handle at an end opposite said pointed end, said handle extending outwardly from another end of said sleeve, said trocar member having a triangular cross-sectional shape within said passageway of said sleeve.

18. The assembly of claim 17, said sleeve having an angularly offset end surface at said one end of said sleeve.

19. The assembly of claim 17, further comprising:

a spacer member removably fastened at an end of said sleeve adjacent said trocar member, said spacer member for sealing said passageway of said sleeve.

* * * * *